United States Patent [19]

Nicolau et al.

[11] 4,407,795

[45] Oct. 4, 1983

[54] INCLUSION COMPOUND OF P-HEXADECYLAMINO BENZOIC ACID IN CYCLODEXTRIN AND METHOD OF USE

[75] Inventors: Gabriela Nicolau, Cliffside Park, N.J.; Alfred P. Tonelli, Nanuet, N.Y.

[73] Assignee: American Cyanamid Company, Stamford, Conn.

[21] Appl. No.: 283,852

[22] Filed: Jul. 16, 1981

[51] Int. Cl.$^3$ ............... A61K 31/73; C08B 37/16
[52] U.S. Cl. ................................ 424/180; 424/310; 424/361; 536/46; 536/103
[58] Field of Search ............... 424/180, 361, 310; 536/46, 103

[56] References Cited

U.S. PATENT DOCUMENTS

| 3,453,257 | 7/1969 | Paramerter et al. | 536/46 |
| 3,453,260 | 7/1969 | Paramerter et al. | 536/103 |
| 3,459,732 | 8/1969 | Hull et al. | 536/46 |
| 3,472,835 | 10/1969 | Buckler et al. | 536/46 |
| 4,066,829 | 1/1978 | Nair et al. | 536/46 |
| 4,100,342 | 7/1978 | Finley | 536/103 |
| 4,311,694 | 1/1982 | Krueger et al. | 424/361 |

OTHER PUBLICATIONS

Albright, et al., "Jour. of Pharmaceutical Science," vol. 68, No. 7, Jul. 1979, pp. 936–937.

Primary Examiner—Johnnie R. Brown
Attorney, Agent, or Firm—Jack W. Richards

[57] ABSTRACT

An inclusion compound of p-hexadecylamino benzoic acid sodium salt in β-cyclodextrin which provides enhanced bioavailability of this antiatherosclerotic agent.

3 Claims, No Drawings

INCLUSION COMPOUND OF P-HEXADECYLAMINO BENZOIC ACID IN CYCLODEXTRIN AND METHOD OF USE

DESCRIPTION OF THE INVENTION

This invention is concerned with an inclusion compound comprising p-hexadecylamino benzoic acid sodium salt in β-cyclodextrin useful as an antiatherosclerotic agent.

The compound p-hexadecylamino benzoic acid sodium salt is described and claimed in U.S. Pat. 3,868,416 together with methods for its preparation. Method of treatment claims for p-hexadecylamino benzoic acid sodium salt are found in U.S. Pat. No. 3,924,001. U.S. Pat. No. 3,974,274 describes derivatives of β-cyclodextrin with utility as hypolipemic agent. U.S. Pat. No. 3,954,787 discloses the use of cyclodextrin as a matrix in the lyophilization of E2 prostaglandins to enhance stability. Acta Pharmaceutica Hungarica, 49, 207–221 (1973), J. Szejtli, et al. describes the use of β-cyclodextrin to enhance the bioavailability of stearic acid and of Indomethacin in the rat. K. H. Fromming and J. Weyermann, Arzneim. Forsch. (Drug Res.) 23, No. 3,424 (1973), discloses increased bioavailability in man of salicylic acid as its β-cyclodextrin inclusion compound. These are also numerous foreign patents on β-cyclodextrin inclusion compounds involving perfumes, deodorants, insecticides and pharmaceuticals, representative of which are: Jap. No. 77-15809; Jap. No. 76-95135; Polish No. 103,276; Ger. No. 2,840,142; Jap. No. 78-142516; Jap. No. 78-133623; Jap. No. 78-109953; Jap. No. 77-114014; Jap. No. 75-29724; Ger. No. 2,260,536; Jap. No. 75-116617; Jap. No. 75-94108; Jap. No. 75-100217; Jap. No. 75-89,516 and Jap. No. 75-64320.

Atherosclerosis is a complex disease involving various kinds of interference with the function of arteries in supplying blood to the vital organs and to the extremities. Interference occurs in the form of narrowing of the lumen of the artery and consequent obstruction of blood flow, in the form of hardening of the arterial wall and resulting loss of the necessary elasticity, or in the form of weakening of the wall due to abnormal processes taking place in the arterial wall, or combinations of these processes. Such pathological changes in the arterial wall, covered by the terms plaque formation of atherosclerotic lesion development, not only interfere with maintenance of healthy body tissue in a direct fashion but also indirectly via thromboembolic complications from dislodged fragments of the plaque or platelet thrombi obstructing arteries. The aorta is the most frequently affected artery and then, in order, the coronary, cerebral, and the major peripheral arteries of the upper and lower extremities.

It has recently been recognized that atheromatous plaque formation is a complex chain of events controlled at different stages by several factors and involving many physiological entities. Arterial injury resulting from mechanical stresses as well as from various immunological, biochemical or chemical actions disrupts the single continuous, innermost layer of endothelical cells that line the artery and form a barrier protecting the adjoining intimal layer of the artery wall from deleterious types or concentrations of blood constituents such as lipoproteins or mitogenic factors. Acute or chronic mechanical stress (such as that caused by high blood pressure) of differing force, types or durations leads to enhanced influx of protein and lipoproteins into the intimal layer of the arterial wall. Also, thrombi forming on the walls of the artery can become incorporated into the arterial wall and provide a nucleus for development of atherosclerotic lesions. Examples of factors causing injury to arterial walls are oxygen deficiency such as from carbon monoxide, high blood pressure, immune reactions such as serum sickness or diseases such as homocystinuria or diabetes. Such injuries cause the development of atherosclerotic lesions of the fibrous and complex type even without the additional stress of elevated serum-lipid concentrations. Although there are variations of the way in which certain factors contribute to the development of the atherosclerotic lesion, there is general acceptance that the atherosclerotic disease process consists of several changes in the cellular and molecular structure of the arterial wall. Smooth muscle cells migrate from the media into the intima and proliferate. Intimal cells ingest large amounts of lipid (particularly cholesterol) and lipid-laden foam cells appear. A large increase of an extracellular matrix consisting of collagen, acidic mucopolysaccharides (glycosaminoglycans), fibrin, and elastin develops. This matrix traps from the blood and immobilizes low-density lipoprotein and its associated cholesterol and cholesterol ester. Cholesterol is also immobilized within the cells of the arterial wall as cholesterol esters by the action of a cholesterol-esterifying enzyme present therein. Inhibition of this enzyme, fatty acyl-CoA: cholesterol acyl transferase (ACAT), is an important therapeutic characteristic of the compounds of the present invention since this enzyme has been shown to play a role in the development of atheromatous plaque. Inhibition of this enzyme is independent of and unrelated to lowering of serum-lipid concentration.

Cholesterol and other lipids are transported in the blood in the form of lipoproteins of several types divided into classes according to their density. The low-density and very low-density lipoproteins are atherogenic in nature and low concentrations of them in blood are the most favorable for health, with respect to atherosclerosis. In contrast, a high concentration of high-density lipo-proteins (HDL) is desirable since the high concentration has been shown to correlate with a low incidence of atherosclerosis. The compound p-hexadecylamino benzoic acid sodium salt which elevates HDL concentrations is therefore therapeutically useful as a result of this antiatherogenic effect.

When the plaque is more complex than that described above as a result of further cellular degenerative changes, hemorrhage and thrombosis, it has the distinctive characteristic of being also calcified to varying degrees, which makes such lesions even more threatening to health. The compound p-hexadecylamino benzoic acid sodium salt which minimizes the calcium deposition in the plaque possesses an important therapeutic characteristic.

Atherosclerosis, the most common cause of coronary artery disease, is of great medical concern since it is especially inclined to occlude those arteries supplying blood to the heart muscles and brain, thereby producing permanent damage to these organs. Such damage may lead to ischemic heart disease, myocardial infarction, congestive heart failure, life-threatening arrhythmias, senility, or even stroke. Involvement of leg arteries may lead to gangrene and loss of the limb.

In the past, attempts to treat atherosclerosis and its sequelae have been confined to lowering the levels of cholesterol, phospholipids, or triglycerides in the blood by the oral administration of various substances which have been generally referred to in the art as hypolipidemic agents or hypocholesteremic adjuvants. Some of such substances are lecithin, pectin, cottonseed oil, corn oil, and the mucilaginous substances listed in U.S. Pat. No. 3,148,114. In addition, several synthetic hypolipidemic agents are now available, namely, clofibrate, probucol, D-thyroxine, cholestyramine, and nicotinic acid [Levy & Frederickson, Postgraduate Medicine 47, 130 (1970)]. Although these agents are effective to varying degrees in lowering blood lipids, none has been demonstrated to inhibit the progression of atherosclerosis as has the compound p-hexadecylamino benzoic acid sodium salt.

Therapy of atherosclerosis can be provided by (1) preventing arterial plaque formation, the consequent occlusion, and the obstruction of blood flow and (2) preventing existing plaques from growing in thickness or in area or from hardening and thus critically increasing the obstruction. It is clear that, in a partially obstructed artery, any further percent of enlargement of existing plaque will produce a larger percentage and a more critical degree of reduction of the already diminished blood flow. Both of the above actions can help to provide the blood flow essential for maintenance of healthy body tissues and keep the flow free enough to adjust to work and exercise needs. A further desirable therapeutic action is the regression of existing plaque, but this action is much more difficult on the complex plaque that is producing symptoms. Regardless of theories as to which facet of atherosclerotic plaque formation is the most critical, what medical science needs are agents which produce the key, previously unattainable therapeutic result—namely, prevention of obstruction of the arteries to the point of interfering with health and threatening life. For the most useful therapy, orally active agents are required since they would be taken for a number of years. Thromboembolic complications of atherosclerosis would be reduced by therapy which minimized plaque formation and decreased the "hardening" process represented by smooth-muscle cell proliferation and deposition of fibrin, collagen, and calcium.

The compound p-hexadecylamino benzoic acid sodium salt was found to give certain desirable therapeutic results. This compound has a novel set of characteristics and actions which produce a highly therapeutic effect on eight aspects of the atherosclerotic disease process and drastically reduce or completely prevent the deposition of the major components of the atherosclerotic plaque. This compound acts directly on the arterial walls in these several ways to keep the arteries open even under conditions where important atherogenic factors are operating and where lipid concentrations in the serum are enormously high compared to normal. The various actions in and on the arterial wall are: reduction of deposition of connective-tissue collagen and elastic-fiber elastin, decreased smooth-muscle cell proliferation, reduced calcium deposition, lowering of the formation of the extracellular matrix and its trapping of very low-density lipoproteins, decreased immobilization of cholesterol in the form of ester from this trapping as well as from cholesterol-esterification by an arterial enzyme inhibited by this compound, and decrease of both the area and the thickness of the plaque, i.e., decreased incidence and severity of plaque formation. A 2-fold increase in the antiatherogenic (high-density) type of lipoprotein in the serum is accompanied by an antiatherogenic decrease in the atherogenic very low-density lipoproteins. Most important is a 2-fold reduction in the luminal narrowing in 4 major coronary arteries. Accompanying this effect on lumen size are increases in myocardial blood flow in the non-stressed and the stressed heart. Reductions in luminal narrowing are seen in major peripheral arteries as well.

The active ingredient of the present invention prevents or diminishes the formation or enlargement of arterial lesions in mammals when administered in amounts ranging from about 2 mg. to about 200 mg. per kilogram of body weight per day. A preferred dosage regimen for optimum results would be from about 2 mg. to about 50 mg. per kilogram of body weight per day, and such dosage units are employed that a total of from about 200 mg. to about 3.5 grams of the active compound for a subject of about 70 kg. of body weight are administered in a 24-hour period. These doses refer to the concentration of p-hexadecylamino benzoic acid sodium salt and do not include the concentration of $\beta$-cyclodextrin. This dosage regimen may be adjusted in the individual case to provide the optimum therapeutic response. For example, several divided doses may be administered daily or the dose may be proportionally reduced as indicated by the exigencies of the therapeutic situation. A decided practical advantage of this invention is that the active compound may be administered in a convenient matter such as the oral or buccal routes or it may be incorporated directly in the diet.

The active ingredient of the present invention may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipients and used in the form of ingestible tablets, buccal tablets, troches, capsules, and the like. Such compositions and preparations should contain at least 0.1% of active compound. The percentage of the compositions and preparation may, of course, be varied any may conveniently be between about 1 to about 60% of the weight of the unit. The amount of active ingredient in such therapeutically useful compositions is such that a suitable dosage will be obtained. Preferred compositions or preparations according to the present invention are prepared so that an oral dosage-unit form contains between about 2 and 200 milligrams of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. Various other materials may be present as coatings or to otherwise modify the physical form of the dosage unit. For instance, tablets, pills, or capsules may be coated with shellac sugar or both. Of course, any material used in preparing any dosage-unit form should be pharmaceutically pure and substantially non-toxic in the amounts employed.

In has now been discovered that an inclusion compound of p-hexadecylamino benzoic acid sodium salt with $\beta$-cyclodextrin provides enhanced bioavailability when compared to p-hexadecylamino benzoic acid sodium salt alone. In contrast β-cyclodextrin has a low absorption and lack of toxicity as described by J. Szejtli, et al., Arzneim. Forsch. (During Research), 30, (1), 808 (1980), wherein it was established that less than 0.01% of β-cyclodextrin was absorbed by man upon oral administration, mainly as glucose formed by enzymatic hydrolysis of β-cyclodextrin.

The inclusion compound contains about 8% p-phexadecylamino benzoic acid sodium salt, corresponding to a β-cyclodextrin/p-hexadecylamino benzoic acid sodium salt molar ratio of about 4:1. The formation of a true inclusion compound is indicated by a constant molar ratio of the components, regardless of their original concentrations and in this instance has been confirmed by powder X-ray diffraction. Radio labeled $^{14}C$ p-hexadecylamino benzoic acid sodium salt was used and the amount included by β-cyclodextrin was determined by scintillation counting, as well as by a fluorometric method. The complex was obtained in 76% yield.

Two bioavailability studies, one in dogs and the other in monkeys were performed to determine relative absorption differences between the following two formulations.

Formulation A

Micromilled $^{14}C$ labeled p-hexadecylamino benzoic acid.

Formulation B

Fourteen grams of β-cyclodextrin is dissolved by stirring in 100 ml. of water of 70°–80° C. A 1.4 g. portion of $^{14}C$ labeled p-hexadecylamino benzoic acid sodium salt is dissolved by stirring in 115 ml. of ethanol at 70°–80° C. The ethanol solution is poured into the aqueous solution with stirring, cooled and the precipitate collected, providing a complex containing 8% p-hexadecylamino benzoic acid sodium salt.

Two dogs were administered capsules containing both formulations at 13 mg. of drug/kg. of body weight in a crossover study, with a three week washout period between the two formulations. The resulting concentration of $^{14}C$ labeled p-hexadecylamino benzoic acid sodium salt in the plasma, measured at various time intervals, are recorded in Table I. Areas under a plasma concentration vs. time curve (AUC) were calculated from the plasma drug concentrations at each time period, by using a basic program and the HP 3354 Lab. Data System. These areas are a measure of drug absorption and indicate an increase in absorption for the p-hexadecylamino benzoic acid sodium salt from Formula B versus Formula A, of about 14% (dog No. 1) and 105% (dog No. 2) respectively. There is less variability between the absorption of Formula B as compared with Formula A.

TABLE I

| Time (Hours) | Plasma Concentration in mcg. equiv. of $^{14}C$ labeled drug/ml. | | | |
|---|---|---|---|---|
| | Dog No. 1 | | Dog No. 2 | |
| | Formula A | Formula B | Formula A | Formula B |
| 0 | 0.12 | — | 0.04 | 0.1 |
| 0.33 | 0.14 | 0.02 | 0.11 | 0.01 |
| 0.5 | 0.32 | 0.19 | 0.21 | 0.07 |
| 1 | 1.04 | 0.45 | 0.48 | 0.04 |
| 2 | 2.73 | 2.25 | 0.87 | 0.77 |
| 3 | 3.30 | 4.56 | 1.48 | 1.90 |
| 4 | 3.70 | 4.85 | 1.14 | 2.40 |
| 5 | 3.31 | 4.06 | 1.11 | 2.25 |
| 6 | 3.15 | 3.82 | 1.10 | 2.39 |
| 8 | 2.31 | 3.26 | 0.67 | 2.41 |
| 12 | 1.62 | 2.16 | 0.61 | 1.43 |
| 24 | 1.49 | 1.19 | 0.45 | 1.07 |
| 48 | 0.70 | 1.06 | 0.12 | 0.51 |
| 72 | 0.55 | 0.68 | 0.18 | 0.27 |
| 96 | 0.51 | 0.48 | 0.21 | 0.32 |
| 120 | 0.41 | 0.35 | 0.29 | 0.12 |
| AUC | 112.56 | 127.82 | 37.42 | 76.75 |

AUC = area under the 0–120 hour plasma concentrations/time curves: mcg. × hour/ml. (per mg./kg. dose)

Monkeys in groups of four were administered either Formulation A or Formulation B in 2% starch suspension by gavage at doses of about 20 mg./kg. The concentration of $^{14}C$ labeled p-hexadecylamino benzoic acid sodium salt in the plasma, measured at various time intervals, are recorded in Table II and it was shown that the mean area under the plasma drug concentration/time curve for the group of monkeys receiving Formula B was 7.38 mcg. × hour/ml. (per mg./kg.) dose while that for the group of monkeys receiving Formula A was 40.01 mcg. hour/ml./mg./kg. This corresponds to an 84% increase in absorption of the $^{14}C$ labeled p-hexadecylamino benzoic acid from Formula B versus Formula A.

TABLE II

| Time (Hours) | Plasma Concentration in mcg. equiv. of $^{14}C$ labeled drug/ml. | | | | | | | |
|---|---|---|---|---|---|---|---|---|
| | Formula A Monkey No. | | | | Formula B Monkey No. | | | |
| | 1 | 2 | 5 | 6 | 3 | 4 | 7 | 8 |
| 0.5 | 0.39 | 4.83 | 3.46 | 0.35 | 0.44 | 0.21 | 0.16 | 1.97 |
| 1 | 1.60 | 8.06 | 6.06 | 1.92 | 3.07 | 1.12 | 0.37 | 13.94 |
| 2 | 5.39 | 12.96 | 5.84 | 4.07 | 18.49 | 5.71 | 9.74 | 27.53 |
| 3 | 6.43 | 11.51 | 3.50 | 3.49 | 17.56 | 11.20 | 7.63 | 12.52 |
| 4 | 6.19 | 11.17 | 2.41 | 4.86 | 14.94 | 12.42 | 7.58 | 7.13 |
| 6 | 4.33 | 8.89 | 1.64 | 4.35 | 9.71 | 10.16 | 3.27 | 4.22 |
| 8 | 2.56 | — | 1.33 | 2.77 | 6.71 | 8.44 | 2.75 | 2.82 |
| 12 | 1.17 | 2.07 | 0.67 | 1.16 | 2.92 | 4.26 | 1.53 | 1.75 |
| 24 | 0.46 | 0.95 | 0.37 | 0.59 | 1.19 | 1.88 | 0.75 | 0.58 |
| 48 | 0.24 | 0.56 | 0.26 | 0.28 | 0.61 | 0.80 | 0.32 | 0.19 |
| 96 | 0.20 | 0.24 | 0.23 | 0.19 | 0.33 | 0.26 | 0.19 | 0.14 |
| Dose (mg./kg.) | 21.08 | 21.08 | 21.08 | 21.08 | 18.20 | 18.20 | 18.20 | 22.75 |
| AUC 0–96 mcg.-hour/ml. (per mg./kg. dose) | 3.32 | 6.97 | 2.53 | 3.22 | 9.63 | 10.17 | 4.71 | 5.01 |
| Mean AUC | 4.01 | | | | 7.38 | | | |

EXAMPLE 1

Preparation of 50 mg. Tablets

| Formulation | |
|---|---|
| 8% p-Hexadecylamino benzoic acid sodium salt-β-cyclodextrin inclusion compound | 625 mg. |
| Sodium starch glycolate | 30–60 mg. |
| Magnesium stearate | 50 mg. |
| | 705–735 mg. |

The inclusion compound and a disintegrating agent such as sodium starch glycolate are blended with sufficient water to provide a granulation. The granulation is screened to size, dried, rescreened to size, a lubricant such as magnesium stearate is added and the mixture is compressed into tablets containing 50 mg. of p-hexadecylamino benzoic acid sodium salt.

We claim:

1. The method of inhibiting atherosclerotic occlusion of the arteries in a mammal which comprises orally administering to said mammal an effective amount of an inclusion compound comprising about 8% p-hexadecylamino benzoic acid sodium salt in β-cyclodextrin in a molar ratio of about 1:4 of said salt to β-cyclodextrin which provides enhanced bioavailability of said salt over said salt orally administered alone.

2. A composition of matter in oral unit dosage form which provides enhanced bioavailability of p-hexadecylamino benzoic acid sodium salt over said salt alone for inhibiting atherosclerotic occlusion of the arteries in a mammal comprising an inclusion compound of about 8% p-hexadecylamino benzoic acid sodium salt in β-cyclodextrin in a molar ratio of about 1:4 of said salt to β-cyclodextrin containing about 2 to 200 milligrams of said salt in each oral unit dosage form in association with a pharmaceutically acceptable carrier.

3. The inclusion compound of about 8% p-hexadecylamino benzoic acid sodium salt in β-cyclodextrin in a molar ratio of about 1:4 of said salt to β-cyclodextrin which provides enhanced bioavailability of said salt over said salt alone.

* * * * *